United States Patent [19]
Bailey et al.

[11] Patent Number: 5,976,136
[45] Date of Patent: Nov. 2, 1999

[54] METHOD AND APPARATUS FOR EXTERNAL BONE FIXATOR

[75] Inventors: Kirk J. Bailey, Andover; Rui J. Ferreira, Newark, both of N.J.

[73] Assignee: Electro Biology, Inc., Parsippany, N.J.

[21] Appl. No.: 09/075,683

[22] Filed: May 11, 1998

[51] Int. Cl.⁶ .................................................. A61B 17/56
[52] U.S. Cl. .................. 606/61; 606/54; 606/61
[58] Field of Search .................. 606/61, 60, 62, 606/59, 58, 54

[56] References Cited

U.S. PATENT DOCUMENTS

| | | | |
|---|---|---|---|
| Re. 31,809 | 1/1985 | Danieletto et al. | 128/92 A |
| 2,391,537 | 12/1945 | Anderson | 128/84 |
| 4,135,505 | 1/1979 | Day | 128/92 A |
| 4,273,116 | 6/1981 | Chiquet | 128/92 A |
| 4,483,334 | 11/1984 | Murray | 128/92 A |
| 4,620,533 | 11/1986 | Mears | 128/92 ZV |
| 4,621,627 | 11/1986 | DeBastiani et al. | 128/92 ZZ |
| 4,714,076 | 12/1987 | Comte et al. | 128/92 ZW |
| 4,745,913 | 5/1988 | Castaman et al. | 128/92 ZW |
| 4,895,141 | 1/1990 | Koeneman et al. | 606/54 |
| 4,944,743 | 7/1990 | Gotzen et al. | 606/61 |
| 4,988,349 | 1/1991 | Pennig | 606/58 |
| 5,152,280 | 10/1992 | Banieli | 606/61 |
| 5,620,442 | 4/1997 | Bailey et al. | 606/64 |
| 5,662,650 | 9/1997 | Bailey et al. | 606/54 |

*Primary Examiner*—Michael Buiz
*Assistant Examiner*—(Jackie) Tan-Uyen Ho
*Attorney, Agent, or Firm*—Harness, Dickey & Pierce, P.L.C.

[57] ABSTRACT

An external fixator for securing a first bone portion in a position relative to a second bone portion. The fixator includes a first clamping assembly for receiving a first bone screw connected to the first bone portion and a second clamping assembly for receiving a second bone screw connected to the second bone portion. The first and second clamping assemblies are interconnected by a main body which includes a plurality of serrated joints. Each serrated joint preferably includes first and second overlapping flanges which carry cooperating serrated surfaces adapted to selectively interlock. Each joint includes a fastener defining a pivot axis, the fasteners being operative to mechanically separate the cooperating serrated surfaces upon rotation in a first direction.

20 Claims, 3 Drawing Sheets

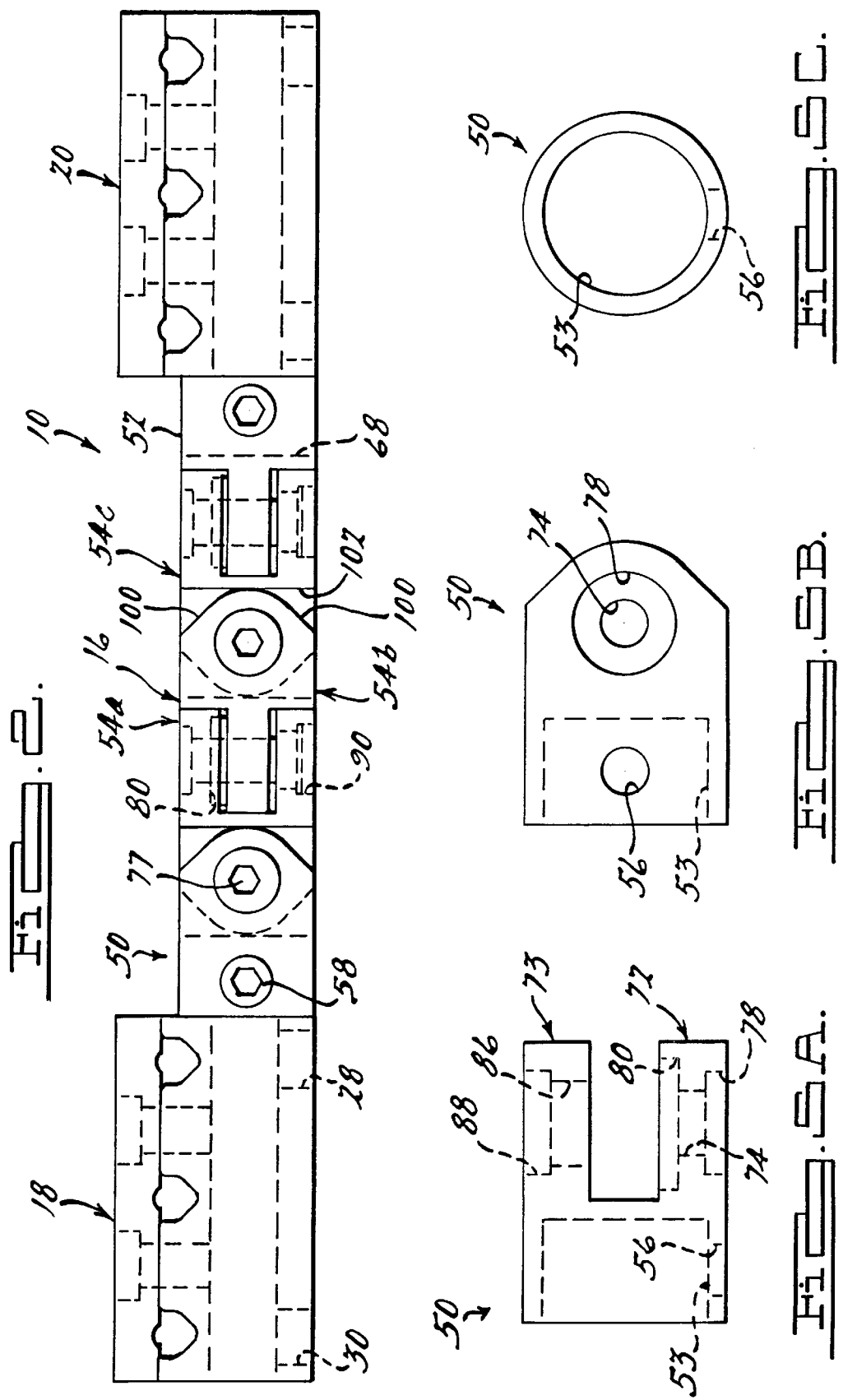

METHOD AND APPARATUS FOR EXTERNAL BONE FIXATOR

BACKGROUND OF THE INVENTION

1. Field of the Invention

The present invention relates generally to orthopedic surgical procedures, and more particularly to a method and apparatus for external fixation of bones.

2. Description of the Related Art

In various orthopedic surgical procedures, it is desired to secure two or more portions of bone in a relatively fixed relationship to each other. This need is often a result of a fracture which has occurred to the bone. To ensure that the bone can properly regenerate and fuse the fractures of the bone, it is important that the various bone portions be fixed at desired positions during bone regeneration. Often, the bone portions can be held in their desired positions with a cast.

Various external fixation devices for the repair of traumatized bone are also known. For example, commonly assigned U.S. Pat. No. 5,620,442 to Bailey et al. discloses an apparatus for the external fixation of small bones. The apparatus is illustrated to generally include a bone screw clamp for receiving a first bone screw which is connected to a first bone portion. The external fixator further includes a bone screw clamp which is operable to receive a second bone screw connected to the second bone portion. The first and second bone screw clamps include a spherical portion. The external fixator further includes a connection member for securing the spherical portions of the bone screw clamps. The connection member defines a radiographic window to permit radiographic examination of the bone fracture without removing the apparatus. U.S. Pat. No. 5,620,442 is hereby incorporated by reference as if fully set forth herein.

While known fixators, including the type described above, have proven to be commercially acceptable for certain applications, they nevertheless can be the subject of improvements.

SUMMARY OF THE PRESENT INVENTION

According to one aspect, the present invention relates to a fixator operable for securing two portions of bone in a fixed relationship to each other, with the first bone portion having a first bone screw attached thereto while the second bone portion has a second bone screw attached thereto. The fixator includes a first bone screw clamping assembly for receiving the first bone screw and a second bone screw clamping assembly for receiving the second bone screw. The fixator further includes a central body interconnecting the first and second bone screw clamping assemblies. The central body includes a plurality of links or knuckles permitting independent rotation of either bone screw clamping assembly about a longitudinal axis of the fixator. The knuckles further provide a plurality of independently lockable serrated joints each establishing a pivot axis substantially perpendicular to the longitudinal axis.

An advantage of the present invention is to provide a method and apparatus for fixation of bones that incorporate a plurality of serrated joints which allow for improved control throughout a range or articulation.

Another advantage of the present invention is to provide a method and apparatus for fixation of bones that permit independent angular adjustment in each of a plurality of perpendicular planes.

It is a related advantage of the present invention to provide a method and apparatus for fixation of bones that incorporate serrated joints which mechanically separate upon loosening of a fastener to allow smooth articulation.

Another advantage of the present invention is to provide a method and apparatus for fixation of bones that incorporate serrated joints with captured fasteners which function to maintain alignment of cooperating serrations and thereby reduce the torque required during operation.

BRIEF DESCRIPTION OF THE DRAWINGS

FIG. 2 is an enlarged elevational view of the apparatus for external fixation of bone according to the teachings of the preferred embodiment of the present invention.

FIGS. 5(A)–(C) are illustrations of a first connector member shown in FIG. 2 according to the teachings of the preferred embodiment of the present invention.

DETAILED DESCRIPTION OF THE PREFERRED EMBODIMENT

The following description of the preferred embodiment of the present invention is merely exemplary in nature and is in no way intended to limit the subject invention or its application or uses.

Figure 1:
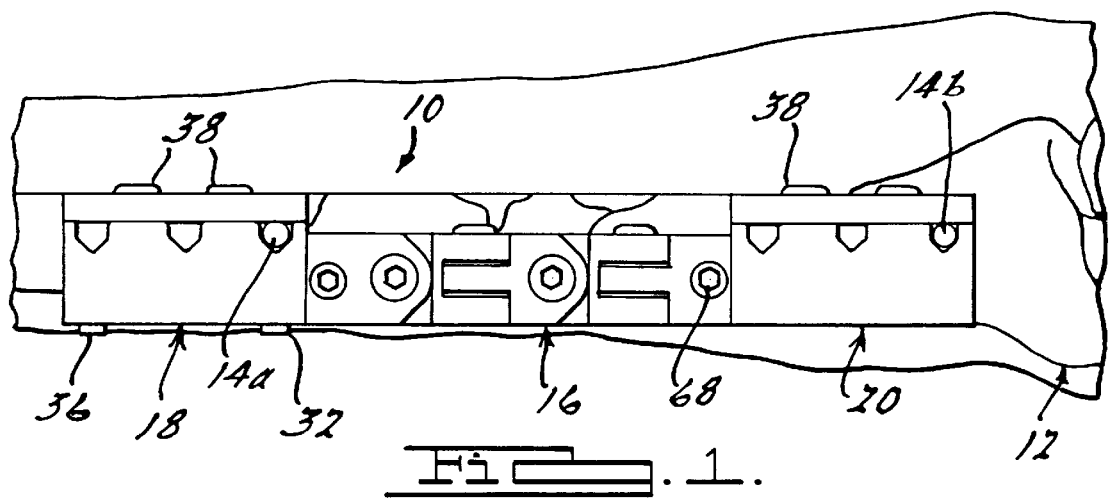
FIG. 1 is an elevational view of the apparatus for external fixation of bones according to the teachings of the preferred embodiment of the present invention shown in operative association with first and second portions of a bone.

Referring initially to FIG. 1, an apparatus 10 for the external fixation of a bone 12 constructed in accordance with the present invention is shown. The apparatus 10 is connected to the bone 12 through at least a first bone screw 14a and a second bone screw 14b, thereby securing spaced apart portions of the bone 12 relative to each other. In the exemplary application illustrated in FIG. 1, the bone shown represents a tibia 12 of a child. However, it is to be understood that the apparatus 10 may be operatively attached to a variety of other types of bones.

With continued reference to FIG. 1 and additional reference to FIG. 2, the apparatus 10 is shown to generally include a main body portion 16 as well as a first bone screw clamping assembly 18 and a second bone screw clamping assembly 20. As will be appreciated below, the main body 16 functions to allow the apparatus 10 to articulate so as to provide a desired orientation of the bone screws 14 with respect to the bone 12. The first bone screw clamping assembly or bone screw clamp 18 is used to secure the first bone screw 14a to the apparatus 10 while permitting the first bone screw 14a to be axially displaced from the main body 18. In a similar fashion, the second bone screw clamping assembly 20 which is also able to secure the second bone screw 14b to the apparatus 10 as well as to allow the second bone screw 14b to be axially displaced with respect to the main body 16.

The first bone screw clamping assembly 18 will be described in greater detail with reference to FIGS. 3(a)–3(c). It is to be understood that while only the first bone screw clamping assembly 18 is being described, the second bone screw clamping assembly 20 will have a similar construction. The first bone screw clamping assembly 18 includes a base portion 22 and a cover portion 24. The base portion 22 serves to receive the first bone screw 14a in one of a plurality of grooves 26, while the cover portion 24 serves to secure the first bone screw 14a within the grooves 26.

As discussed in detail in U.S. Pat. No. 5,662,650, the grooves 26 include two contact surfaces which are substantially planar so as to permit line contact of the first bone screw 14a in two positions within the grooves 26. Since the first bone screw 14a also engages the cover portion 24 of the bone screw clamp 18, the first bone screw 14a engages the first bone screw clamp 18 in three positions (i.e., along the contact surfaces as well as on the cover portion 24). This provides line contact for the bone screw 14 which secures the bone screws 14 in a more effective manner than if the grooves 26 were cylindrical.

The base portion 22 of the bone screw clamping assembly 18 further includes a first aperture 28 (shown in phantom) and a second aperture 30 (also shown in phantom). The first aperture 28 is used to receive a threaded member 32 (shown in FIG. 1) which serves to secure a rail member 34 in a locked position as will be more fully discussed below. The second aperture 30 is also used to receive a threaded member 36 (shown in FIG. 1) which is able to secure a compression/distraction member (not shown). One suitable compression/distraction member is described in connection with the external fixator disclosed in U.S. Pat. No. 5,662,650.

The cover portion 24 of the first bone screw clamping assembly 18 is secured to the base portion 22 of the first bone screw clamping assembly 18 by means of two screws 38. To accommodate these screws 38, the cover portion 24 of the bone screw clamping assembly 18 includes two apertures 40 (shown in phantom in FIGS. 3A and 3B) which mate with corresponding apertures 42 in the base portion 22 of the bone screw clamping assembly 18. Accordingly, upon secured threaded engagement of the screws 42 within the apertures 38, the cover portion 24 of the bone screw clamping assembly 18 may be secured to the base portion 22 of the bone screw clamping assembly 18.

Figures 4A, 4B, 4C:
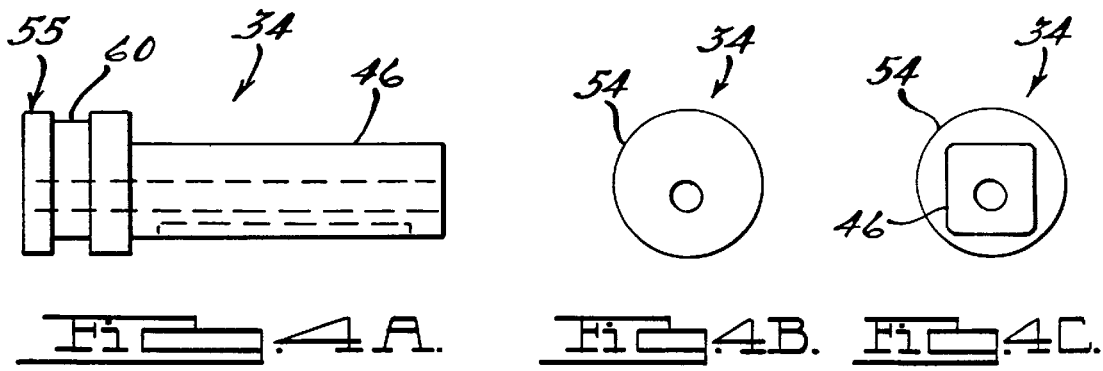
FIGS. 4(A)–(C) are illustrations of a rail member shown in FIG. 2 according to the teachings of the preferred embodiment of the present invention.

To provide means for laterally displacing the first bone screw clamping assembly 18 with respect to the main body or central body 16, the bone screw clamping assembly 18 further includes a rail member 34. The rail member 34 is illustrated in FIGS. 4A–4C to include a rectangular-shaped extension 46 which is able to receive in a rectangular-shaped bore 48 of the bone screw clamp 18. Because of the cross-sectional shape of the rectangular-shaped extension 46, the base portion 22 of the bone screw clamp 18 is able to slide on the rectangular-shaped extension 46 of the rail member 34, though the base portion 22 is unable to rotate with respect to the rectangular-shaped extension 46.

To provide means for displacing the second bone screw clamping assembly 20 with respect to the main body 16, the second bone screw clamping assembly 20 similarly includes a rail member (not specifically shown). As with the rail member 34 associated with the first bone screw clamp 18, the rail member associated with the second bone screw clamp 20 has a rectangular-shaped extension which is able to receive a rectangular-shaped bore of the second bone screw clamp 20.

The components of the main body 16 will now be described in greater detail. As will become apparent, the main body 16 includes a plurality of knuckles which define a plurality of pivot axes oriented perpendicular to one another. FIGS. 1 and 2 illustrate the apparatus 10 to include five (5) knuckles which will be introduced below with reference numerals 50, 52 and 54a–54c. Depending on the particular application, the apparatus 10 may alternatively include more than five (5) knuckles or less than five knuckles. The plurality of knuckles of the main body 16 of the present invention is specifically shown to include first and second connection members 50 and 52, respectively, as well as a first, second and third rotational components 54a, 54b, and 54c. The first and second connection members 50 and 52 serve to secure the main body 16 to the rail members 34.

To provide means for allowing 360° rotation of the first bone screw clamping assembly 18 about a longitudinal axis of the apparatus 10, the first connection member 50 includes a female recess 53 for receiving a male extension 55 of the rail member 34. The first connection member 50 includes an internally threaded aperture 56 which intersects the female recess 53. The internally threaded aperture 56 is adapted to receive a set screw 58 which engages a reduced diameter groove 60 formed in the male extension 55. Upon initial tightening of the set screw, the first connection member 50 and the rail member 34 are rotatably joined. Further rotation of the set screw 58 arrests relative rotation of the rail member 34 and the first connection member 50.

Figure 7A:
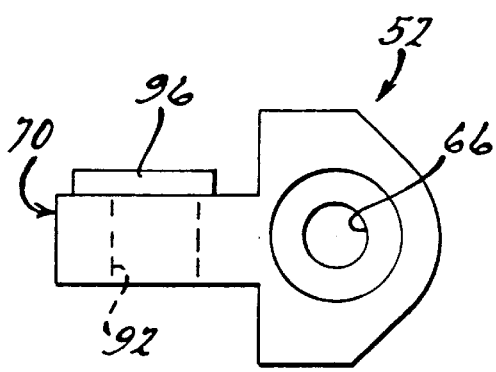
FIGS. 7(A)–(B) are illustrations of a second connection member shown in FIG. 2 according to the teachings of the preferred embodiment of the present invention.
Figure 7B:
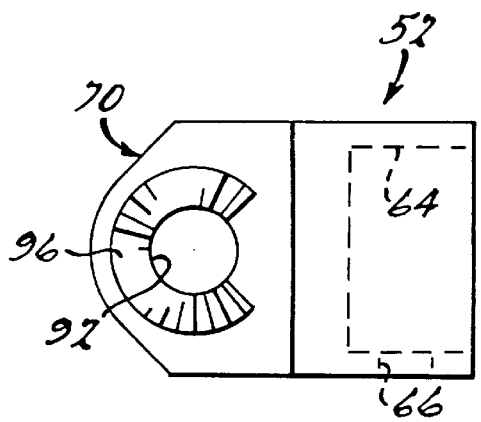

With reference to FIGS. 7A–7B, the second connection member 52 is similarly shown to include a female recess 64 for receiving a male extension (not shown) of the rail member associated with the second bone screw clamp 20. Again, the second connection member 52 includes an internally threaded aperture 66 which intersects a female recess 64 and is adapted to receive a set screw 68 for selectively engaging the rail member.

Figure 6A:
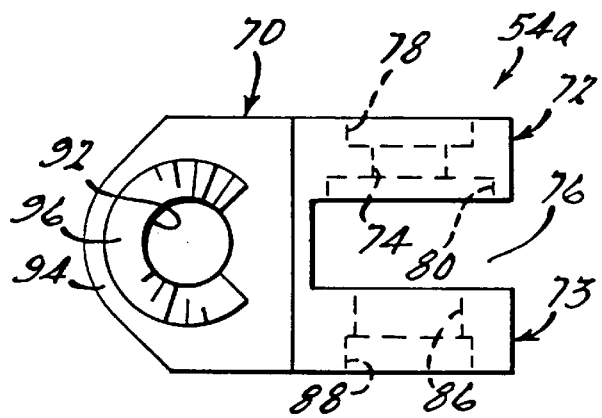
FIGS. 6(A)–(B) are illustrations of a rotational component shown in FIG. 2 according to the teachings of the preferred embodiment of the present invention.
Figure 6B:
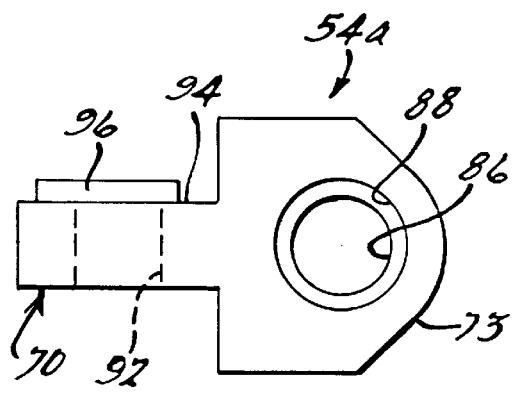

With reference to FIGS. 6A and 6B, the first rotational component 54a will be described. It is to be understood that while only the first rotational component 54a is being described, the second and third rotational components 54b and 54c will have similar constructions. To provide means for establishing a plurality of serrated joints, each of the rotational components 54 includes a male joint portion and a female joint portion. For example, the first rotational component 54a is shown to include a male portion comprising a male flange 70 and a female portion having first and second spaced apart flanges 72 and 73. The first and second spaced apart flanges 72 and 73 define a recess or opening 76.

The first flange 72 includes an unthreaded aperture 74 for receiving a fastener 77. The aperture 74 includes a countersunk portion 78 for accepting a head of the fastener 77 and a recess 80 for receiving a base 81 of a locking washer 82 (shown in FIGS. 8A–8B). The locking washer 82 has a plurality of locking teeth or serrations 84. The second flange 73 includes an aperture 86 having a countersunk portion 88 for accepting a lock nut 90 (shown in FIG. 1) which limits translation of the fastener 77 and prevents the fastener 77 from inadvertent removal. Again, it will be understood that the second and third rotational components 54b and 54c include substantially identical female portions. The first connection member 50 also includes a substantially identical female portion. Common reference numerals are used to identify common elements throughout the drawings.

As shown in the drawings, the male flange 70 of the first rotational component 54a is adapted to be received in the recess 76 of the female portion of the first connection member 50. The flange 70 includes an internally threaded aperture 92 for receiving the threaded fastener 77. A surface 94 of the flange 70 is formed to include a plurality of locking teeth or serrations 96 radially extending from the center of the aperture 92 which are adapted to cooperate with the serrations 84 of the locking washer 82 for positively locating the first rotational component 54a relative to the first connector member 50 at a selected one of a plurality of angular positions.

The second and third rotational components 54b and 54c include substantially identical male flanges 70. The second connection member 52 also includes a substantially identical male flange 70. Again, common reference numerals are used to identify common elements throughout the drawings.

Tightening of the fastener 77 serves to draw the first flange 72 of the first connection member 50 and the flange 70 of the first rotational component 54a together, thereby causing the locking washer 82 and plurality of locking teeth 96 to arrest relative rotation. Because the threaded fastener 77 is threadably engaged only with the internally threaded aperture 92 of the flange 70 and translation of the lock nut 90 is limited, loosening of the threaded fastener 77 mechanically separates the flange 70 from the first flange 72 and thereby displaces the locking washer 82 and the plurality of locking teeth 96. As a result, smooth relative movement of the components is allowed.

In the preferred embodiment, the shank of the fastener 77 is closely toleranced with the aperture 74 of the flange 72 and the locking nut 90 is closely toleranced with the countersunk portion 78. As a result, alignment between cooperating serrations 84 and 96 is maintained. By virtue of such alignment, the torque required to arrest relative rotation between adjacent knuckles is reduced.

To provide means for limiting relative angular movement between adjacent components of the central body 18, the first and second flanges 72 and 73 of each female portion are formed to include a pair of substantially linear stop surfaces 100 adapted to abut a stop flange 102 on an adjacent component. For example, the stop surfaces 100 of the first rotational component 54a cooperate with a stop flange 102 on the first connection member 50. The stop surfaces 100 and stop flange 102 cooperate to limit relative rotation at a predetermined angle. In the exemplary embodiment, 45° of relative rotation in two opposite directions (e.g. 90° of angulation) is permitted.

The foregoing discussion discloses and describes merely exemplary embodiments of the present invention. One skilled in the art will recognize from such discussion and from the accompanying drawings and claims, that various changes, modifications and variations can be made therein without departing from the spirit and scope of the invention. For example, while the exemplary application of the subject invention fixes the relative positions of two portions of a common bone, certain teachings of the present invention may be applied to external fixators which interconnect two different bones.

What is claimed is:

1. An apparatus for securing a first bone portion in a fixed relationship to a second bone portion, the apparatus comprising:
   a first bone screw operable to be connected to the first bone portion;
   a second bone screw operable to be connected to the second bone portion;
   a first clamping assembly receiving said first bone screw;
   a second clamping assembly receiving said second bone screw;
   an adjustable central body interconnecting said first clamping assembly and said second clamping assembly, said central body including a first connector member and a second connector member, said first connector member interconnected to said first clamping assembly and having a female portion, said second connector member interconnected to said second clamping assembly and having a male portion, said central body further including at least one rotational member having a male portion and a female portion, said male portion of said at least one rotational member interconnected to said female portion of said first connector member, said female portion of said at least one rotational member interconnected to said male portion of said second connector member.

2. The apparatus for securing a first bone portion in a fixed relationship to a second bone portion of claim 1, wherein said at least one rotational member includes a first rotational member, said male portion of said first rotational member is directly attached to said female portion of said first connector member.

3. The apparatus for securing a first bone portion in a fixed relationship to a second bone of claim 1, wherein said at least one rotational member includes a first and a second rotational member, both of said first and second rotational members having a male portion and a female portion.

4. The apparatus for securing a first bone portion in a fixed relationship to a second bone of claim 1, wherein said at least one rotational member includes at least three rotational members, each rotational member having a male portion and a female portion, said male portion of each rotational member being pivotally attached to one of said female portion of said first connector member and said female portion of an adjacent rotational member, said female portion of each rotational member being pivotally attached to one of said male portion of said second connector member and said male portion of an adjacent rotational member.

5. The apparatus for securing a first bone portion in a fixed relationship to a second bone of claim 1, wherein said central body defines a plurality of pivot axes equal in number to one more than the number of rotational members.

6. The apparatus for securing a first bone portion in a fixed relationship to a second bone of claim 5, wherein each of said plurality of pivot axes is independently lockable.

7. The apparatus for securing a first bone portion in a fixed relationship to a second bone of claim 6, wherein said plurality of pivot axes are mutually perpendicular.

8. An apparatus for securing a first bone portion in a fixed relationship to a second bone portion, the apparatus comprising:
   a first bone screw operable to be connected to the first bone portion;
   a second bone screw operable to be connected to the second bone portion;
   a first clamping assembly for clamping said first bone screw;
   a second clamping assembly for clamping said second bone screw;
   a central body having a longitudinal axis, said central body including at least one joint including first and second serrated portions being selectively interlockable, and means for mechanically separating said first and second serrated portions to permit smooth articulation of said at least one joint.

9. The apparatus for securing a first bone portion in a fixed relationship to a second bone portion of claim 8, further comprising first rotational means for allowing rotation of said first clamping assembly about said longitudinal axis and a second rotational means for allowing rotation of said second clamping assembly about said longitudinal axis.

10. The apparatus for securing a first bone portion in a fixed relationship to a second bone portion of claim 9, wherein said at least one joint is interdisposed between said first rotational means and said second rotational means.

11. The apparatus for securing a first bone portion in a fixed relationship to a second bone portion of claim 8, wherein said at least one joint includes a plurality of joints.

12. The apparatus for securing a first bone portion in a fixed relationship to a second bone portion of claim 11, wherein said plurality of joints defines a corresponding plurality of pivot axes, said pivot axes being substantially mutually perpendicular.

13. The apparatus for securing a first bone portion in a fixed relationship to a second bone portion of claim 11, wherein said plurality of joints defines a corresponding plurality of pivot axes, each of said pivot axes being independently lockable.

14. The apparatus for securing a first bone portion in a fixed relationship to a second bone portion of claim 11, wherein said plurality of joints defines a corresponding plurality of pivot axes, each of said pivot axes being substantially perpendicular to said longitudinal axis.

15. An apparatus for securing a first bone portion in a fixed relationship to a second bone portion, the apparatus comprising:

a first bone screw operable to be connected to the first bone portion;

a second bone screw operable to be connected to the second bone portion;

a first clamping assembly for receiving the at least one bone screw;

a second clamping assembly for receiving the plurality of bone screws; and a central body having at least one joint defining a pivot axis, each said joint including a first member and a second member, said first member including first and second flanges which are spaced apart, said first flange having a serrated portion and an unthreaded aperture, said second flange including an unthreaded aperture, said second member having a third flange interdisposed between said first and second flanges, said third flange having a threaded aperture aligned with said unthreaded apertures of said first and second flanges, said third flange further including a serrated portion adapted to selectively interlock with said serrated portion of said first flange, each said joint further including a threaded fastener passing through said unthreaded aperture and threadably engaging said threaded aperture and a lock nut disposed in said second flange for limiting travel of said fastener, said threaded fastener operable to mechanically separate said serrated portion of said first flange and said serrated portion of said third flange upon rotation in a first direction.

16. The apparatus for securing a first bone portion in a fixed relationship to a second bone portion of claim 15, wherein said fastener is further operable to interlock said serrated portion of said first flange and said serrated portion of said third flange upon rotation in a second direction and thereby prevent relative movement between said first flange and said third flange.

17. The apparatus for securing a first bone portion in a fixed relationship to a second bone portion of claim 15, wherein said at least one joint includes a plurality of joints defining a corresponding plurality of pivot axes.

18. The apparatus for securing a first bone portion in a fixed relationship to a second bone portion of claim 15, wherein said at least one joint includes at least three joints defining at least three pivot axes.

19. The apparatus for securing a first bone portion in a fixed relationship to a second bone portion of claim 17, wherein said plurality of pivot axes are mutually perpendicular.

20. The apparatus for securing a first bone portion in a fixed relationship to a second bone portion of claim 17, wherein said apparatus includes a longitudinal axis, and further wherein each of said plurality of pivot axes are substantially perpendicular to said longitudinal axis.

* * * * *

UNITED STATES PATENT AND TRADEMARK OFFICE
CERTIFICATE OF CORRECTION

PATENT NO.     : 5,976,136
DATED          : November 2, 1999
INVENTOR(S)    : Kirk J. Bailey, Rui J. Ferreira It is certified that error appears in the above-identified patent and that said Letters Patent is hereby corrected as shown below:

Title page,
Under References Cited, U.S. PATENT DOCUMENTS, "Banieli" should be -- Danieli --

Figure 8A:
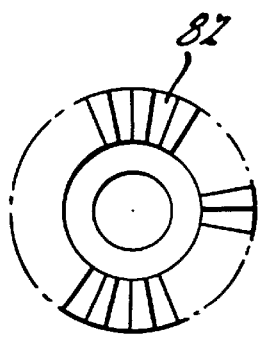
FIG. 8 are illustrations of a locking member shown in FIG. 2 according to the teachings of the preferred embodiment of the present invention.
Figure 8B:
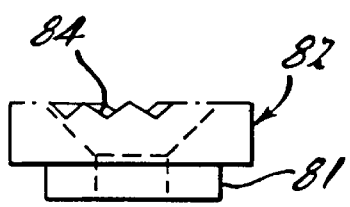

Column 2,
Line 35, "FIG. 8" should be -- FIGS. 8(A)-(B) --

Figures 3A, 3B:
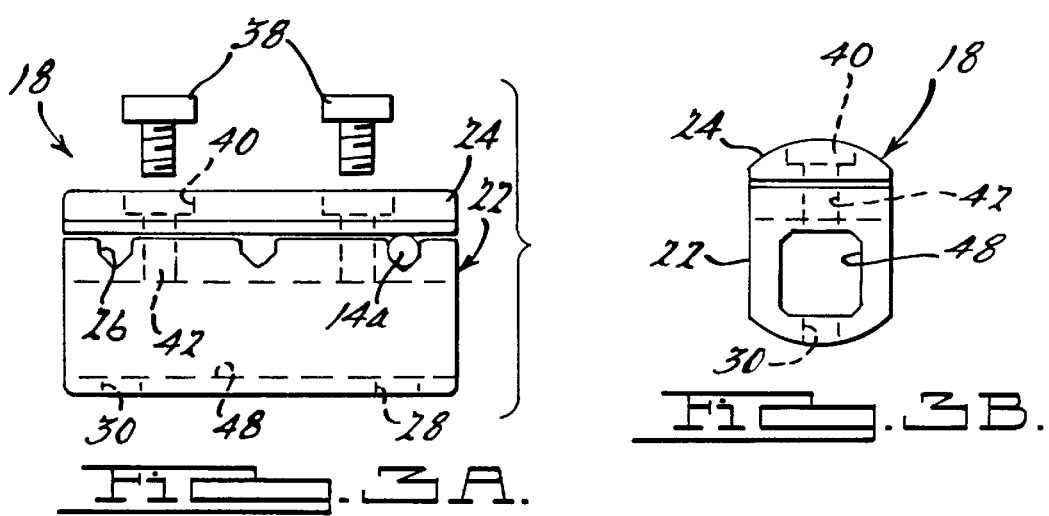
FIGS. 3(A)–(B) are illustrations showing the central body of the bone screw clamping assembly shown in FIG. 2 according to the teaching of the preferred embodiment of the present invention.

Column 3,
Line 6, "FIGS. 3(a)-3(c)" should be -- FIGS. 3(A)-3(C) --

Signed and Sealed this

Twenty-sixth Day of February, 2002

Attest:

JAMES E. ROGAN
Attesting Officer — Director of the United States Patent and Trademark Office